(12) United States Patent  (10) Patent No.: US 8,136,946 B2
Reed  (45) Date of Patent: Mar. 20, 2012

(54) APPARATUS FOR DETERMINING PRESCRIPTION FOR PRISM LENSES FOR DIPLOPIC PATIENTS

(76) Inventor: Roger Glenn Reed, Indianapolis, IN (US)

( * ) Notice: Subject to any disclaimer, the term of this patent is extended or adjusted under 35 U.S.C. 154(b) by 0 days.

(21) Appl. No.: 13/229,831

(22) Filed: Sep. 12, 2011

(65) Prior Publication Data

US 2012/0038887 A1    Feb. 16, 2012

Related U.S. Application Data

(63) Continuation-in-part of application No. 12/854,373, filed on Aug. 11, 2010.

(51) Int. Cl.
*A61B 3/04* (2006.01)
*A61B 3/10* (2006.01)
*A61B 3/02* (2006.01)

(52) U.S. Cl. ......... 351/229; 351/205; 351/222; 351/227

(58) Field of Classification Search ................. 351/229, 351/205–206, 210, 221–226, 200, 227
See application file for complete search history.

(56) References Cited

U.S. PATENT DOCUMENTS 5,104,214 A * 4/1992 Sims ............................. 351/235
5,335,419 A * 8/1994 Marshall ........................... 33/28

* cited by examiner

*Primary Examiner* — Dawayne A Pinkney

(57) ABSTRACT

An apparatus is provided for finding and defining a prescription for prism glasses for Diplopic patients and AMD patients whose Macula and Fovea are damaged enough that the patients have double vision, but, still have relatively good acuity. The apparatus positions lenses in infinitely variable locations horizontally and vertically in front of the patient's eyes until the patient indicates that he/she sees the two images fuse. The H-V coordinates of the location of the Optic center of each lens axis in relation to the patient's visual axis are decentration dimensions indicated for each eye by the H and V dials on the apparatus and are thus the basis for an accurate prescription for prism lenses.

6 Claims, 10 Drawing Sheets

RIGHT-EYE LENS    LEFT-EYE LENS

RIGHT EYE, OD   LEFT EYE, OS

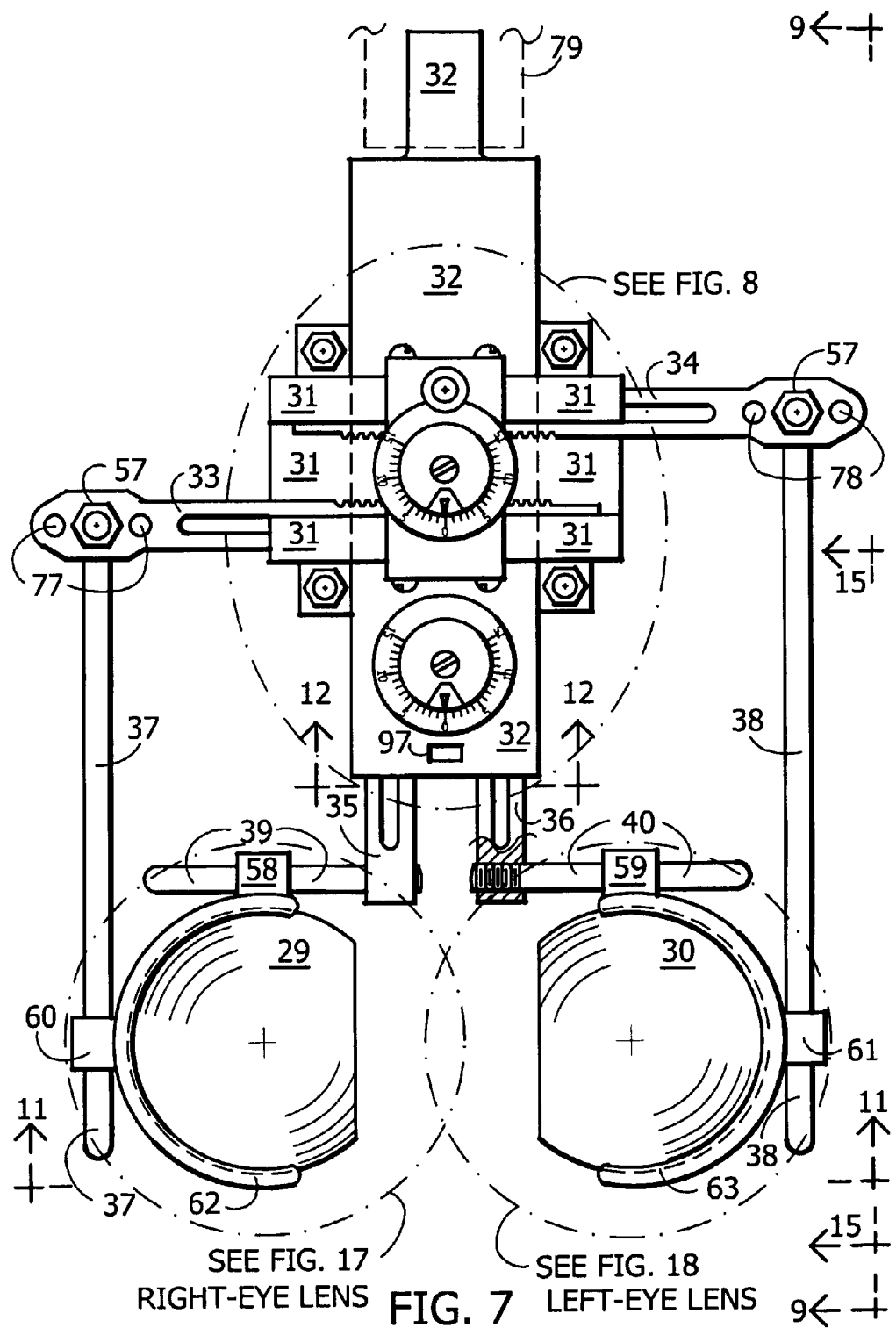
FIG. 7 RIGHT-EYE LENS LEFT-EYE LENS (ENLARGED 2X)

(ENLARGED 2X)

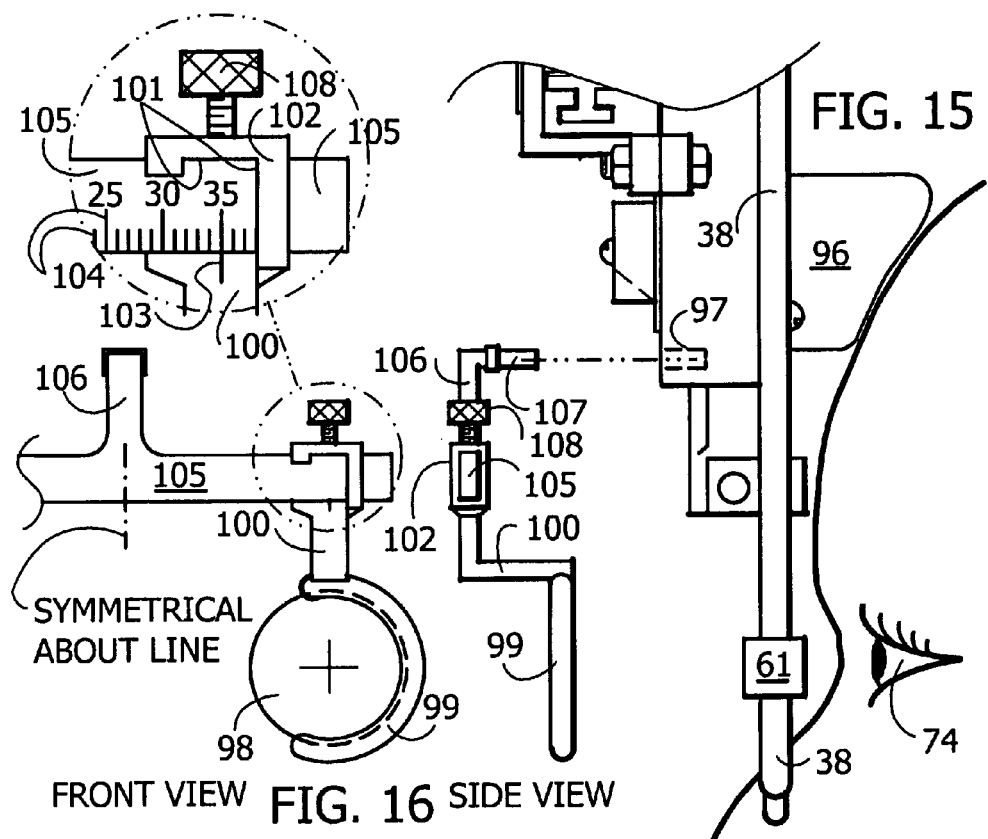
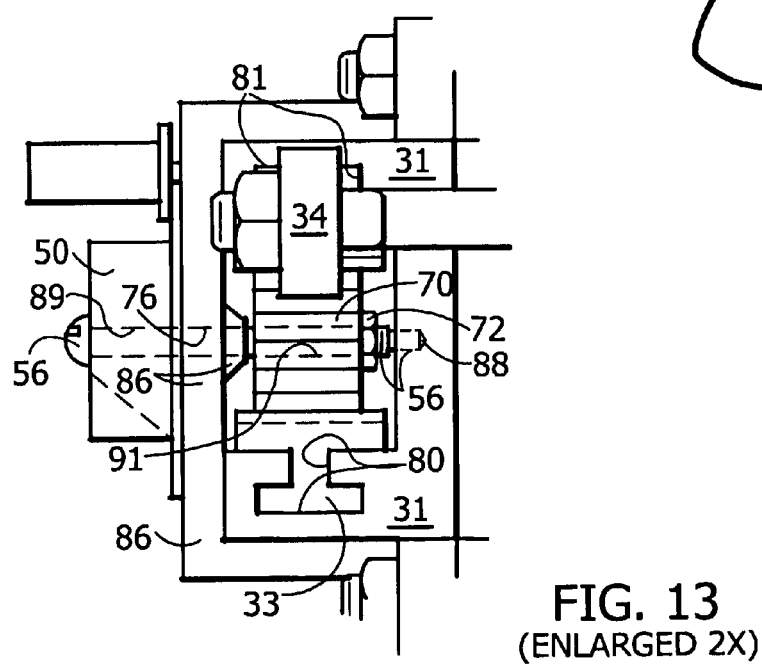

(ENLARGED 2X)

(ENLARGED 2X)
OS

FIG. 19

| HOW TO SELECT LENSES FOR THE PREFERRED EMBODIMENT/PATIENT ||||||||
|---|---|---|---|---|---|---|
| PATIENT'S UNAIDED VISION | PRISM CORRECTION FOR NEAR VISION (READING) ||| PRISM CORRECTION FOR FAR VISION (DRIVING) |||
| NOTES: | A | B | C | A | B | C |
| NEARSIGHTED | (eye) | (biconcave lens) Note 1 | | (eye) | (biconcave lens) Note 2 | |
| FARSIGHTED | (eye) | (biconvex lens) Note 3 | | (eye) | (biconvex lens) Note 4 | (biconcave lens) Note 5 |
| NORMAL-SIGHTED | (eye) | (biconvex lens) Note 6 | (biconcave lens) Note 7 | (eye) | (biconvex lens) Note 6 | (biconcave lens) Note 7 |

NOTES:
A Orientation of Patient's eye in relation to lens(es).
B Movable lens in lens holder of Apparatus, creating prism by decentration.
C Lens in stationary lens holder of the Apparatus - to cancel unwanted magnification.
1 Minus Diopter lens with power for near vision to induce prism by decentration.
2 Minus Diopter lens with power for far vision to induce prism by decentration.
3 Plus Diopter lens with power for near vision to induced prism by decentration.
4 Plus Diopter lens, with power for near vision, to induce prism by decentration.
   Usually this lens will be used in conjunction with a minus lens (Note 5) of the same power for far vision.
5 Minus Diopter lens with same power as lens in Note 4 to cancel the magnification effect to allow far vision.
6 Plus Diopter lens, with power to induce prism by decentration. Usually this lens will be used
   in conjunction with a minus lens (Note 7) of the same power to cancel unwanted magnification.
7 Minus Diopter lens with same power as lens in Note 6 to cancel unwanted magnification.

APPARATUS FOR DETERMINING PRESCRIPTION FOR PRISM LENSES FOR DIPLOPIC PATIENTS

CROSS REFERENCE TO RELATED NON-PROVISIONAL APPLICATION

This Continuation-In-Part (CIP) application claims the benefit of the filing date of U.S. Non-Provisional patent application Ser. No. 12/854,373 filed on Aug. 11, 2010 and titled "Apparatus for Determining Prescription for Reading Lenses for Eyes with Mild AMD", which is hereby incorporated in this CIP.

LEXICON

Generally, equations and terminology familiar to Opticians are used throughout these Specifications.

Lens-blank means a round, polished lens that is edged to fit the lens-holders of the preferred embodiment.

Lens-set means two (OD and OS) lenses of each diopter power specified and plus and/or minus diopter specified.

Integral applied to components of the preferred embodiment, means that a component, that is said to be integral to a larger component, already named and defined, is cast with the said named component as a single homogeneous piece that can not be separated into individual parts.

BACKGROUND

Many people suffering from Adult-onset Macular Degeneration (AMD) have damage to the Macula that has repositioned the Fovea (center of the Macula) causing a new visual-axis to be slightly offset from the original (normal) visual-axis. This is very common in older people. The result, in many cases, is Diplopia. Double vision occurs when the image that one eye sees does not coincide with the image that the other eye sees when looking with both eyes at the same time at the same physical object, making it appear that there are two of everything in the field of view of the Macula and Fovea. The brain can accommodate for slight differences, but, when the offset becomes too great for the brain to accommodate-double vision results. Peripheral vision is not affected by AMD.

Many AMD patients still have relatively good acuity in the AMD eye but the offset of the visual-axis still results in double vision. For patients with AMD in both eyes, the result most likely will be double vision. Another cause of double vision is Strabismus of which there are several types and which sometimes is a result of the right and left eye muscles' inability to coordinate to focus in on an object and make the two images fuse. Double vision sufferers have to find their own method of coping with the problem. For some people, surgery is the answer. For the other people, one way to cope is to close one eye while viewing. This quickly becomes tiring. Another method is to wear an eye-patch instead of closing the eye. The eye-patch interferes with eyeglasses making that option also unsatisfactory. A problem with both methods is that the person loses the peripheral vision in that eye. Losing peripheral vision can actually be dangerous if the person is in a dangerous industrial setting, or driving a vehicle where it is important to see danger approaching with the periphery of one's vision. One crude method of addressing the problem has been the use of Prism Bars held in front of one eye by Ophthalmologists to guess at the amount of induced prism required in eyeglass lenses by the patient to bring the two images together as one. That method is not accurate and has been the source of much dissatisfaction on the part of patients as well as the Ophthalmologists. There are also hand held rotary prisms available. Here again hand held means not very accurate.

Thus, there has always been a need for a more accurate and satisfactory way of improving the seeing ability of such individuals.

SUMMARY

I have had AMD for a number of years and relied on the methods mentioned in the BACKGROUND above and found them to be very unsatisfactory. I was constantly on the lookout for a way that was better. I noticed one day, while using a magnifying glass, that as the magnifying glass is moved across a page in one direction that the words on the printed page appeared to move in the opposite direction. Well, that was not news to me. What was new was me thinking that there may be a new way to use the prism effect. So I theorized that if my reading glasses lens were relocated within their frames, let's say move one up and out (away from the nose) and the other one down and out in infinitely variable distances and combinations, that at some point an image of an object would focus on the center of each Fovea of my two eyes. In other words, the images might be relocated just the exact distance and direction to fuse and appear to me as one image (single vision) instead of two images (double vision) for each object viewed. Through experimentation I found my theory to be correct. As a matter of fact, it worked even better than I had hoped. So, it became obvious to me that there was a need for an apparatus that could quickly and accurately determine what those distances and directions are for any Diplopic patient. Those distances and directions plus the diopter strengths (and other requirements of the eye) would then be the prescription for eyeglass lenses for a Diplopic patient. Hereinafter those distances and directions are referred to as "offset distances (H-V coordinates)". Ideally the apparatus should be infinitely variable within its limits, and would split the induced prism equally but oppositely between the two lenses, to provide maximum accuracy and comfort.

BRIEF DESCRIPTION OF THE DRAWINGS

FIG. 7 is an orthographic front view of the preferred embodiment employing the principles of the present invention.

FIG. 13 is a partial side view taken from FIG. 9.

FIG. 15 illustrates a forehead-rest that steadies the embodiment in relation to the patient's eyes. It is attached to the patient's side of the embodiment with adhesive to a transparent gear-cover.

FIG. 16 illustrates an adjustable eyeglass frame (Front View, Side View and partial enlarged view) for holding stationary lenses for patients who require a negative (−) lens in addition to a prism lens to obtain the necessary magnification for the intended purpose

FIG. 19 is a Table titled HOW TO SELECT LENSES FOR THE PREFERRED EMBODIMENT/PATIENT with notes A through C and 1 through 7 which explain the use of the Table.

DETAILED DESCRIPTION

Figures 9, 10:
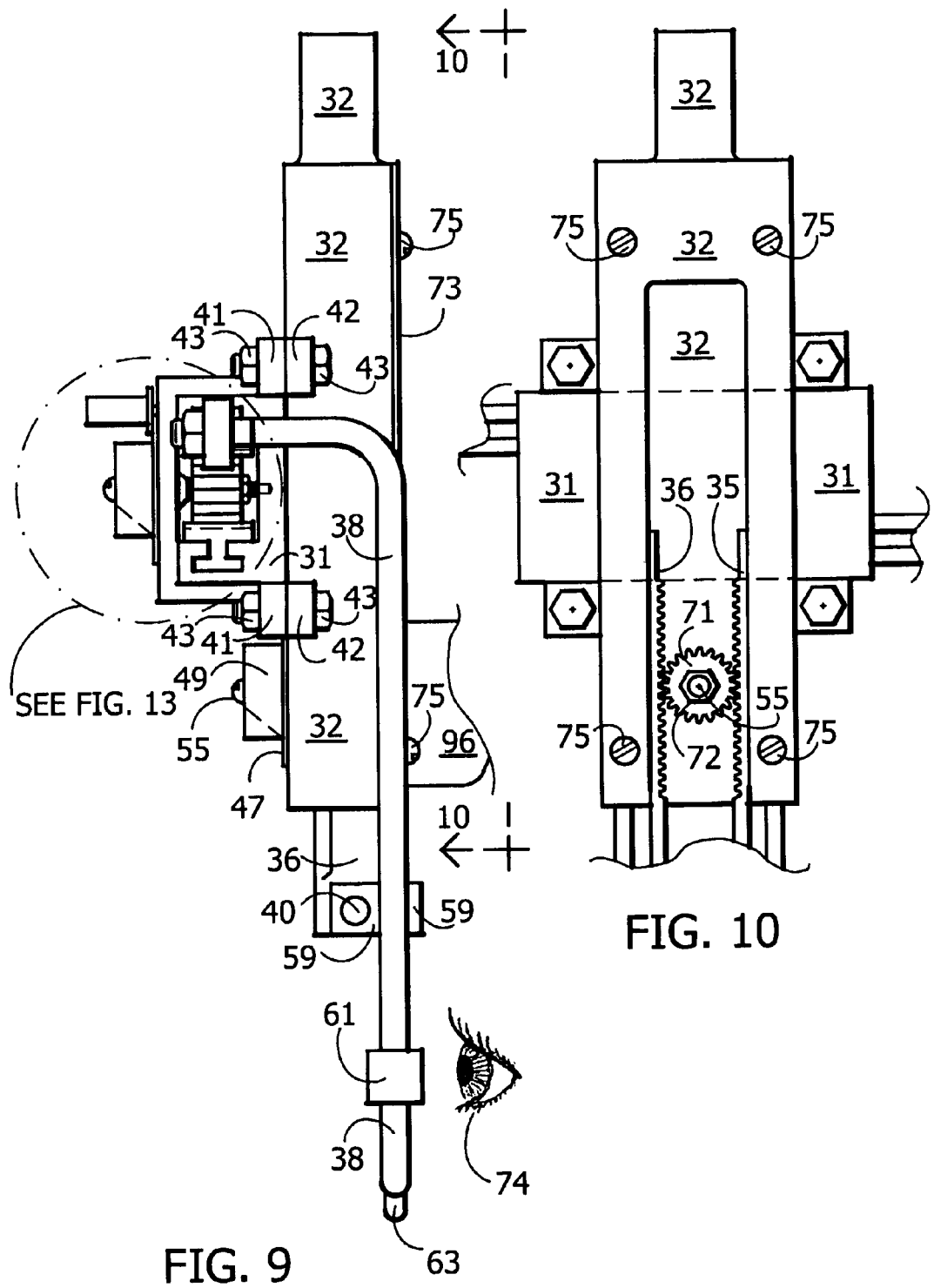
FIG. 9 is an orthographic side view of the preferred embodiment employing the principles of the present invention.
FIG. 10 is a partial orthographic back view of the preferred embodiment employing the principles of the present invention.

All references to "right" and "left" in these Specifications and Claims are relative to the patient's perspective while viewing through a right lens 29 and a left lens 30 shown in FIG. 7, the front view of the preferred embodiment, also further clarified by the graphic of a patient's-eye 74 shown in FIG. 9, a side view.

Like referenced elements are represented by like reference numbers throughout the drawings. Referenced components shown in a particular Figure but not described therein under that Figure's heading is because the referenced component has already been described in detail in a discussion of a previous Figure.

Figure 1:
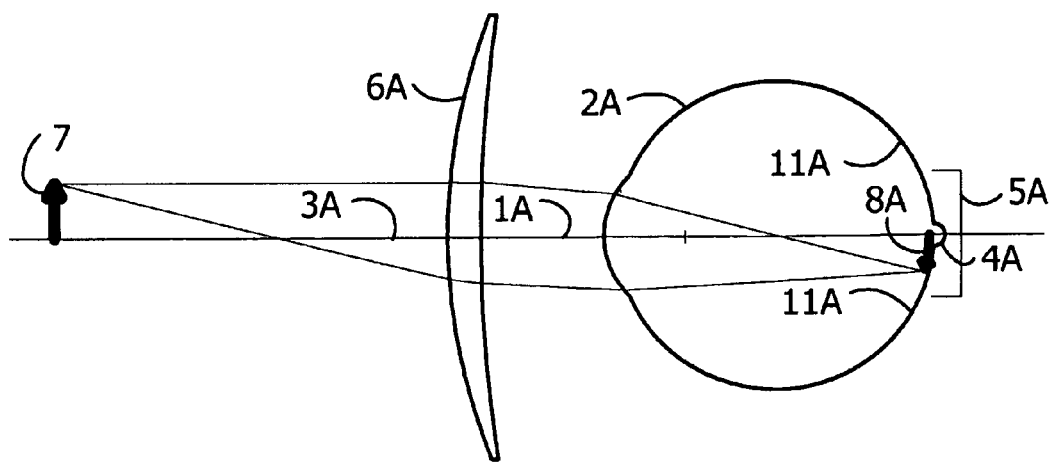
FIG. 1 is a side orthographic view of a normal eye (Emsley Standard Reduced 60-diopter eye), except for farsightedness, viewing an object through a magnifying lens.

FIG. 1 is a side orthographic view of a normal eye (Emsley Standard Reduced 60-diopter eye) hereinafter referred to as ESR60-DE 2A, and it is assumed that it is normal except for farsightedness. Here it is shown viewing an object 7 through a first-magnifying-lens 6A the diopter strength of which has been determined by a conventional eye exam. A first-image 8A of the object 7 is formed upside down on a first-Fovea 4A and surrounding first-Macula 5A (size exaggerated for clarity). Surrounding the first-Macula 5A is a first-Retina 11A.

For the purpose of illustrating how the first-image 8A is formed, light rays emanating from the object 7, and a first-magnifying-lens-axis 3A, and a first-visual-axis 1A are also shown.

Figure 2:
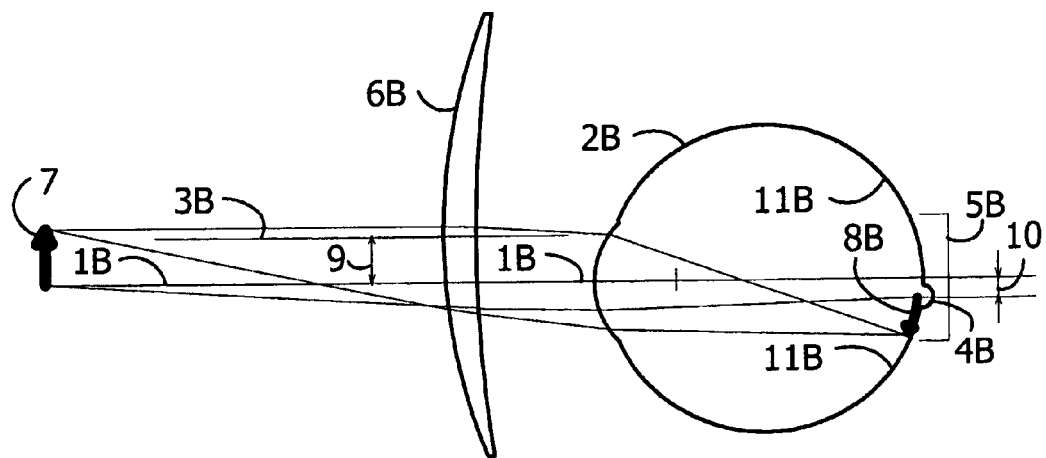
FIG. 2 is a side orthographic view of an eye (Emsley Standard Reduced 60-diopter eye) with farsightedness and AMD, viewing an object through a magnifying lens.

FIG. 2 is an orthographic side view of an eye (Emsley Standard Reduced 60-diopter eye) hereinafter referred to as AMD-ESR60-DE 2B, and it is assumed that in addition to farsightedness it is affected by AMD. Here it is shown viewing the object 7 through a second-magnifying-lens 6B. In this view the effects of AMD has shifted a second-Fovea 4B downward a small second-distance 10. A second-magnifying-lens-axis 3B of the second-magnifying-lens 6B is shifted upward an exact first-distance 9 required to cause a second-image 8B to form on the center of the second-Fovea 4B and (if large enough), on a second-Macula 5B which will make the object 7 appear to be in the same location in space as the normal eye (without AMD) sees it. Surrounding the second-Macula 5B is a second-Retina 11B. Thus with both eyes focusing on the object 7 the two images fuse.

If the second-magnifying-lens-axis 3B were to be aligned with a second-visual-axis 1B, that existed prior to the onset of AMD, then with both eyes open, the patient would see two separate objects 7 (one above the other). This is the case because the image formed in AMD-ESR60-DE 2B would not be centered on the second-Fovea 4B as it is in ESR60-DE 2A, thus the patient would see two objects 7 that do not fuse (coincide).

Where a negative diopter lens is required for the patients eye, the image will be shifted in a direction that is opposite to the direction of a positive diopter lens.

Figure 3:
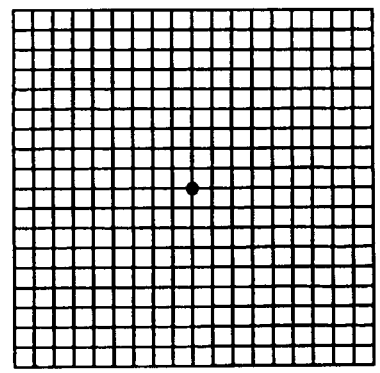
FIG. 3 is a graphic representation of how a standard Amsler Grid looks to a pair of normal eyes. It also represents how a standard Amsler Grid looks to a pair of eyes, one or both of which have mild AMD, but are viewing through corrective lenses embodying the principles of the present invention.

FIG. 3 is a graphic representation of how a standard Amsler Grid looks to a pair of normal eyes. It also represents how a standard Amsler Grid looks to a pair of eyes in which one or both of them has mild AMD but are viewing through prism lenses embodying the principles of the present invention. The Amsler Grid may appear slightly blurry due to mild loss of acuity caused by AMD, but the lines will appear straight. Prism lenses inherently introduce slight blurring caused by dispersion.

Figure 4:
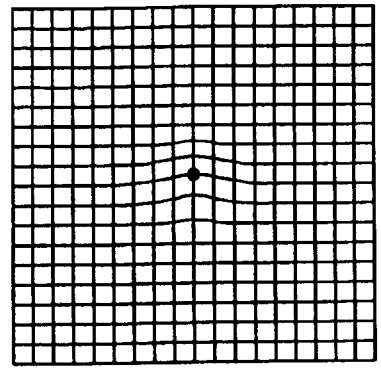
FIG. 4 is a graphic representation of how a standard Amsler Grid might look to an eye with mild AMD where the Fovea (center of the Macula) has shifted slightly downward creating a new visual-axis slightly offset from the original normal visual-axis.

FIG. 4 is a graphic representation of how the standard Amsler Grid might look to an eye with mild AMD, such as AMD-ESR60-DE 2B, viewing through an ordinary magnifying lens, where the Fovea 4B (center of the Macula) has shifted downward the small second-distance 10 away from the normal second-visual-axis 1B.

Figures 5, 6:
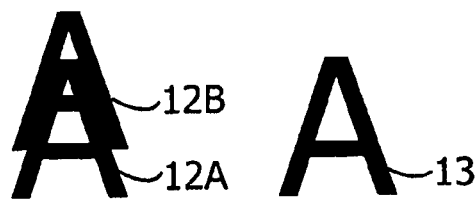
FIG. 5 is a graphic representation of how the alphabetical character "A" might look to a person with Strabismus or with mild AMD in one or both eyes viewing with both eyes through ordinary reading lenses.
FIG. 6 is a graphic representation of how the alphabetical character "A" will look to a person with normal vision viewing with both eyes. It also represents how the alphabetical character "A" might look to a pair of eyes with Strabismus or in which one or both of them has mild AMD but are viewing through corrective lenses embodying the principles of the present invention.

FIG. 5 is a graphic representation of how the alphabetical character "A" might look to a person viewing it with both eyes where one eye has a mild case of AMD such as AMD-ESR60-DE 2B, in which the Fovea 4B has shifted slightly downward away from the normal visual-axis 1B. The other eye could be normal such as ESR60-DE 2A or it could have mild AMD like AMD-ESR60-DE 2B but with the offset in a different direction and/or a different distance. A tiny shift is accommodated for by the brain which makes the viewer see only one "A", but eventually as the distortion becomes greater and greater, the brain can no longer accommodate so that the viewer then sees double. In this case, one "A" above another.

FIG. 6 is a graphic representation of how the alphabetical character "A" will look to a person with normal vision in both eyes. The images formed on the first-Fovea 4A and the first-Macula 5A of the two eyes fuse and appear to the viewer as one object. It also represents how the alphabetical character "A" might look to a pair of eyes in which one or both of them has mild AMD but are viewing through prism lenses made using the principles of the present invention. The image may appear slightly blurry due to mild loss of acuity due to AMD and blurring due to dispersion.

Although the present inventor was able to make a pair of reading glasses by trial and error by using the principles of the present invention and the scientific principles described in FIG. 1 and FIG. 2, there needed to be an apparatus employing the principles of the present invention that would provide a quicker and more accurate way to find and define a prescription (Rx) for prism lenses. The present inventor did conceive such an apparatus and it is the "preferred embodiment" shown in the Drawings, FIG. 7 through FIG. 13 and FIG. 15 through FIG. 18. Plain spherical lenses with a diopter strength appropriate for a patient could be positioned in lens holders in front of the patient's eyes by an apparatus having an infinitely variable graduated horizontal control that moves the pair of lens holders slowly in front of the patients eyes equal distances but in opposite directions and, independently from the horizontal control, an infinitely variable graduated vertical control could slowly move the lens holders in front of the patients eyes equal distances but in opposite directions. The horizontal control could be operated until the patient sees two vertical lines fuse, then the vertical control could be operated until the patient sees two horizontal lines fuse-induced prism by decentration. The numbers on the controls would then be the basis for a prism Rx for the patient. The preferred embodiment described herein satisfies all of those criteria.

Figure 8:
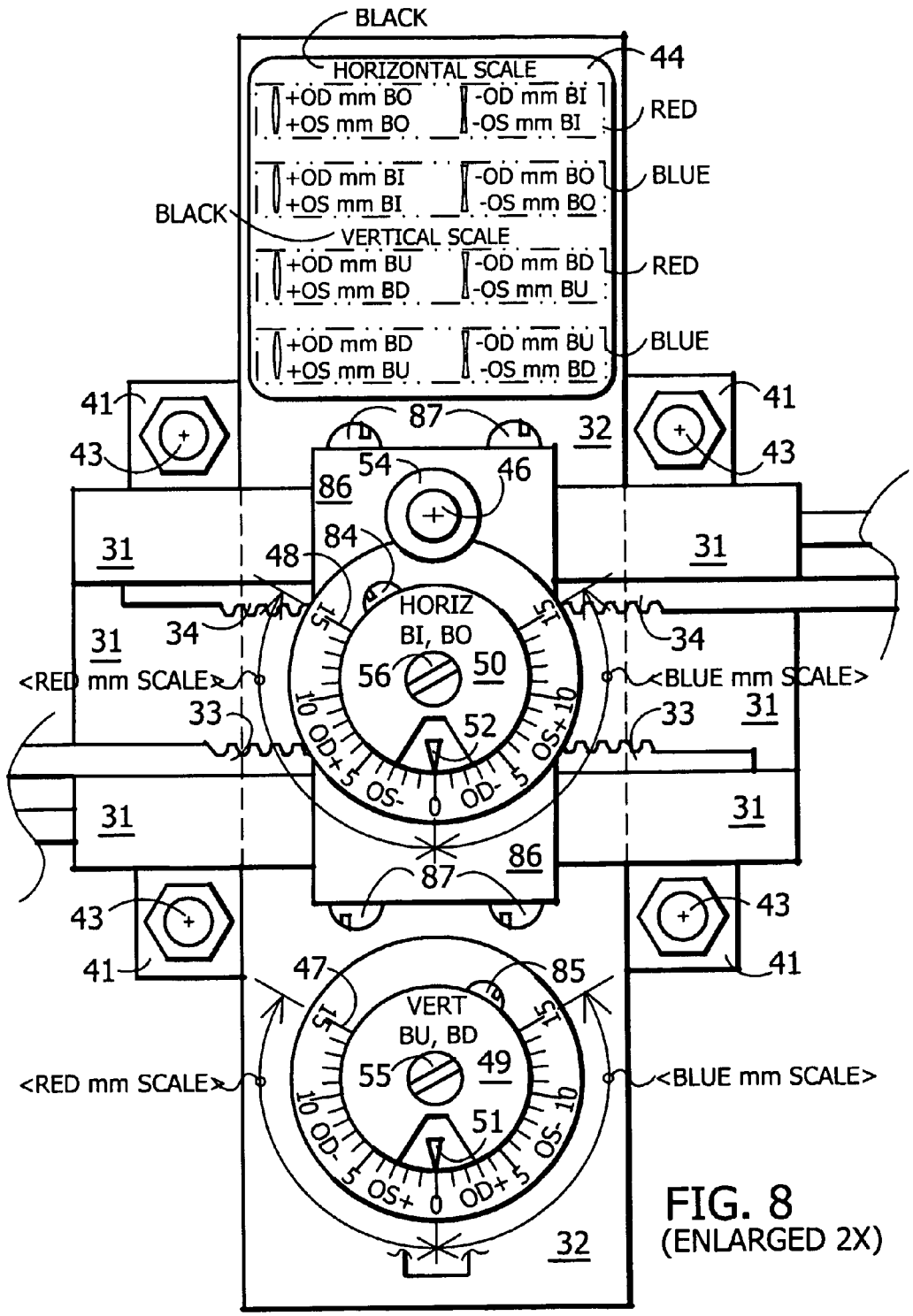
FIG. 8 is an enlarged partial front view of the preferred embodiment employing the principles of the present invention.

FIG. 7 and FIG. 8 illustrate the front view and a partial enlarged front view respectively of the preferred embodiment, employing the principles of the present invention. Components pertinent to the discussion of FIG. 7 and FIG. 8 but that are more clearly shown in other Figures are so noted. The front view clearly shows linkages between a horizontal-adjustment-knob 50 (a first human interface) and a user selectable right-lens-blank 29. Likewise linkages between the horizontal-adjustment-knob 50 and a user selectable left-lens-blank 30 are shown. A vertical-adjustment-knob 49 (a second human interface) is shown linked to the right-lens-blank 29. Likewise linkages between the vertical-adjustment-knob 49 and the left-lens-blank 30 are shown. These linkages provide the basic motions necessary for the lenses, but, more detail is provided below for greater clarity.

Horizontal Control: Horizontal movement of the right-lens-blank 29 begins with the horizontal-adjustment-knob 50 that has a first-central-hole 89 (FIG. 13) along its axis sized to accept a horizontal-pinion-axle 56 that passes through the first-central-hole 89 (FIG. 13) and is prevented from rotating within the horizontal-adjustment-knob 50 by a first-setscrew 84. Further, the horizontal-pinion-axle 56 passes through a slip-fit-hole 76 (FIG. 13) in a bearing-plate 86 and through a horizontal-pinion 70 (FIG. 13) and finally terminates in a bearing-hole 88 (FIG. 13) in a horizontal-guide 31. The bearing-plate 86 is held in place with four bearing-plate-fasteners 87. A locknut 72 (FIG. 13) on the horizontal-pinion-axle 56 confines the horizontal-pinion 70 (FIG. 13) to it's required position on the horizontal-pinion-axle 56. The portion of the horizontal-pinion-axle 56 that fits within the horizontal-pinion 70 (FIG. 13) is non-round in cross section matching a non-round-hole 91 (FIG. 13) in the center of the horizontal-pinion 70 (FIG. 13) whereby any rotation of the horizontal-adjustment-knob 50 results in an equal rotation of the horizontal-pinion 70 (FIG. 13).

The horizontal-guide 31 has a bottom-horizontal-T-shaped groove 80 (FIG. 13) and a top-horizontal-T-shaped-groove 81 (FIG. 13) running parallel to each other and spaced apart far enough to accommodate a bottom-horizontal-rack 33 and a top-horizontal-rack 34, each respective rack has a T-shaped cross section that matches and engages the T-shaped grooves in the horizontal-guide 31 wherein the horizontal-pinion 70 (FIG. 13) is juxtaposed between and engages both the bottom-horizontal-rack 33 and the top-horizontal-rack 34 causing them to slide equal distances but in opposite directions when the horizontal-adjustment-knob 50 is rotated.

A right-vertical-rod 37 is fixedly attached to a right end of the bottom-horizontal-rack 33 through the use of a vertical-rod-fastener 57 and two right-lateral-stability-pins 77 integral to the right-vertical-rod 37 and the right-vertical-rod 37 is vertically slidably connected to a right-vertical-rod-bushing 60 which is integral to a right-lens holder 62 so that the right-lens-holder 62 is free to slide vertically along the length of the right-vertical-rod 37 when it is propelled to do so by a right-horizontal-rod 39, but its horizontal movement is restrained by the right-vertical-rod 37. The end result of the foregoing detailed linkages is that horizontal motion of the bottom-horizontal-rack 33 imparts an equal motion to the right-lens-holder 62.

A left-vertical-rod 38 is fixedly attached to a left end of the top-horizontal-rack 34 through the use of the vertical-rod-fastener 57 and two left-lateral-stability-pins 78 integral to the left-vertical-rod 38 and the left-vertical-rod 38 is vertically slidably connected to a left-vertical-rod-bushing 61 which is integral to a left-lens holder 63 so that the left-lens-holder 63 is free to slide vertically along the length of the left-vertical-rod 38 when it is propelled to do so by a left-horizontal rod 40, but its horizontal movement is restrained by the left-vertical-rod 38. The end result of the foregoing detailed linkages is that horizontal motion of the top-horizontal-rack 34 imparts an equal motion to the left-lens-holder 63.

Figure 12:
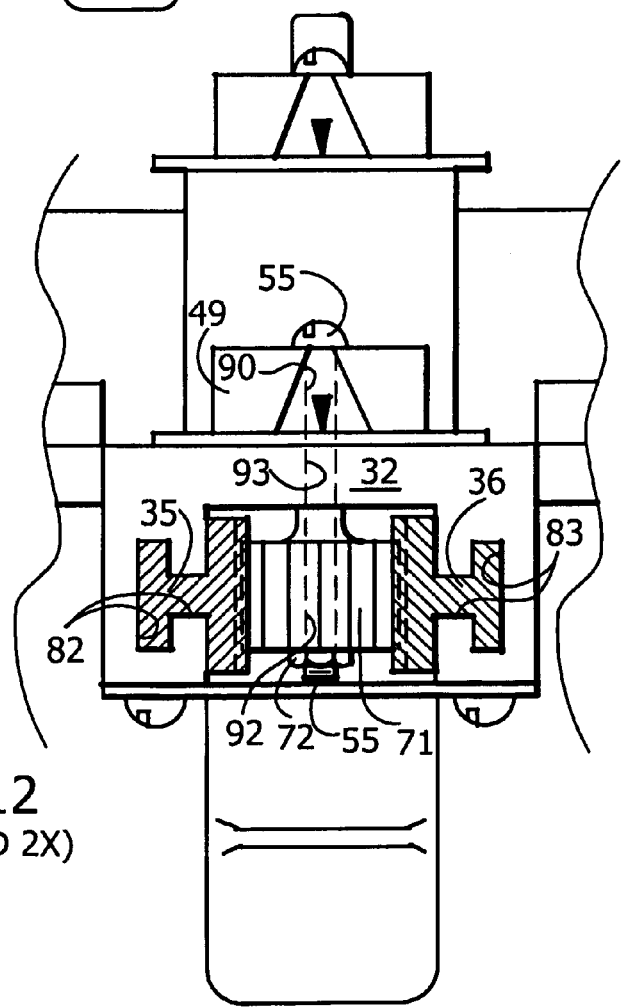
FIG. 12 is a section taken horizontally through FIG. 7, looking up.

Vertical Control: Vertical movement of the right-lens-blank 29 begins with the vertical-adjustment-knob 49 that has a second-central-hole 90 (FIG. 12) along its axis sized to accept a vertical-pinion-axle 55 that passes through the second-central-hole 90 and is prevented from rotating within the vertical-adjustment-knob 49 by a second-setscrew 85. Further, the vertical-pinion-axle 55 passes through a second-slip-fit-hole 93 (FIG. 12) in a vertical guide 32 and through a vertical-pinion 71 (FIG. 12). The locknut 72 (FIG. 12) on the vertical-pinion-axle 55 confines the vertical-pinion 71 (FIG. 12) to its required position on the vertical-pinion-axle 55. The portion of the vertical-pinion-axle 55 that fits within the vertical-pinion 71 (FIG. 12) is non-round in cross section matching a non-round-hole 92 (FIG. 12) in the center of the vertical-pinion 71 (FIG. 12) whereby any rotation of the vertical-adjustment-knob 49 results in an equal rotation of the vertical-pinion 71 (FIG. 12).

The vertical-guide 32 has a right-vertical-T-shaped-groove 82 (FIG. 12) and a left-vertical-T-shaped-groove 83 (FIG. 12) running parallel to each other and spaced apart far enough to accommodate a right-vertical-rack 35 and a left-vertical-rack 36, each respective rack has a T-shaped cross section that matches and engages the T-shaped grooves in the vertical-guide 32 wherein the vertical-pinion 71 (FIG. 12) is juxtaposed between and engages both the right-vertical-rack 35 and the left-vertical-rack 36 causing them to slide equal distances but in opposite directions when the vertical-adjustment-knob 49 is rotated.

The right-horizontal-rod 39 is tightly threaded into a bottom end of the right-vertical-rack 35 and the right-horizontal-rod 39 is horizontally slidably connected to a right-horizontal-rod-bushing 58 which is integral to the right-lens-holder 62 so that the right-lens-holder 62 is free to slide horizontally along the length of the right-horizontal-rod 39 when it is propelled to do so by the right-vertical-rod 37, but its vertical movement is restrained by the right-horizontal-rod 39. The end result of the foregoing detailed linkages is that vertical motion of the right-vertical-rack 35 imparts an equal motion to the right-lens-holder 62.

The left-horizontal-rod 40 is tightly threaded into a bottom end of the left-vertical-rack 36 and the left-horizontal-rod 40 is horizontally slidably connected to a left-horizontal-rod-bushing 59 which is integral to the left-lens-holder 63 so that the left-lens-holder 63 is free to slide horizontally along the length of the left-horizontal-rod 40 when it is propelled to do so by the left-vertical-rod 38, but its vertical movement is restrained by the left-horizontal-rod 40. The end result of the foregoing detailed linkages is that vertical motion of the left-vertical-rack 36 imparts an equal motion to the left-lens-holder 63.

Crosshairs and Lens-holders: The user selectable right-lens-blank 29 is forced into a groove in the right-lens-holder 62 and is held in place by tension due to the right-lens-holder 62 having a slightly smaller diameter than the right-lens-blank 29 by an amount sufficient to prevent the right-lens-blank 29 from falling out; likewise for the left-lens-blank 30 and the left-lens-holder 63.

Zeroing: It is important to provide a pair of plano lenses with crosshairs thereon in the set of lenses that are provided for use in conjunction with the preferred embodiment. A zeroing thumbscrew 46 (FIG. 8) is loosened. With the lenses in place the right-lens-blank 29 and the left-lens-blank 30 can be accurately centered on the patient's eyes. This is done by adjusting a spacing of the pair of crosshairs by rotating the horizontal-adjustment-knob 50 until the spacing of the pair of crosshairs matches a spacing of the patient's P.D.

Figure 14:
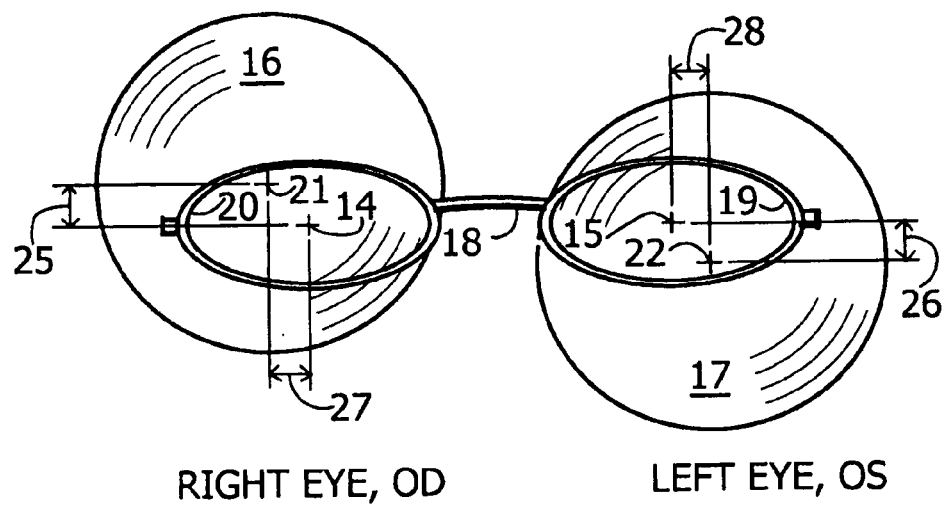
FIG. 14 illustrates how the decentration (H-V coordinates) obtained from an examination of a Diplopic patient's eyes, using the preferred embodiment employing the principles of the present invention, become the Rx and then are translated into the actual orientation of each respective lens-axis in relation to the patient's visual-axis.

At this point (after aligning crosshairs with eyes) a rotatable circular horizontal-scale 48 (FIG. 8) is rotated until zero on the scale aligns with a single horizontal-index 52 printed on the horizontal-adjustment-knob 50 and the zeroing-thumbscrew 46 is tightened thereby clamping the horizontal-scale 48 between a washer 54 and the bearing-plate 86. This is called "zeroing" the scale and splits the horizontal "offset" distance (determined during an examination of a patient) equally but oppositely between the right and left lenses. FIG. 14 provides more detail regarding offset (decentration).

Lens Sets: Lens sets for use in conjunction with the lens-holders 62 and 63 of the Preferred Embodiment generally include the most popular centered-lens diopters in both plus and minus powers. These lenses 29 and 30 are edged to fit the lens holders 62 and 63 and have a segment removed from them to prevent interference when the two lenses are moved toward each other. In that position (centers of the lenses closer than the patient's P.D.), the two flat parts of the lenses face each other allowing the centers of the lenses to be closer together without interference. If the patient's eyes are such that the centers of the lenses must be located farther apart than the patient's P.D., the flat parts of the lenses are rotated away from each other so that there will be more viewable lens area available. Decentered lens sets are also provided for use in conjunction with the lens-holders 62 and 63 of the Preferred Embodiment and generally include the most popular Diopters in both plus and minus powers for each of at least three sub-sets of decentered lenses of varying degrees of decentration up to and a maximum of 70 mm of decentration. These lenses 29 and 30 are edged to fit the lens holders 62 and 63. Lens sets for use in conjunction with the lens-holders 99 of the Preferred Embodiment generally include the most popular centered lens diopters in minus powers. These lenses 98 are smaller than the lenses 29 and 30.

User Instructions: The horizontal-scale 48 and the vertical-scale 47 are both circular scales with millimeter indications ranging from zero to fifteen on each side of a zero. On both scales the right side numerals and indexes are red and on the left side are blue. This is a color code for use with a user-instructions 44 that clearly indicates whether a number on the horizontal-scale 48 aligned with the horizontal-index 52 is indicating a distance that is BI or BO for the patient's OD and BI or BO for the patient's OS. Likewise for a number aligned with the vertical-index 51, the color code in the instructions 44 indicates whether the distance is BU or BD for the patient's OD and BU or BD for the patient's OS.

Interfacing with an articulated arm: A top extension of the vertical-guide 32 is formed to accept a fitting on a commercially available articulated-arm 79 (FIG. 7) that can be used for positioning the preferred embodiment in front of the patient's eyes. See FIG. 9 for a description of four front-lugs 41 and four lug-fasteners 43.

FIG. 9 illustrates the side view of the preferred embodiment, employing the principles of the present invention. A transparent-gear-cover 73, and transparent-gear-cover-fasteners 75 are described under FIG. 10. A human eye 74 is self explanatory. This is the best view in which to discuss the means for securely fastening the horizontal-guide 31 to the vertical-guide 32. Four front-lugs 41 are provided integral to the horizontal-guide 31 flush with the back side of the horizontal-guide 31. These lugs align with four back-lugs 42 provided integral to the vertical-guide 32 which are flush with the front side of the vertical-guide 32. All four pairs of lugs are fastened together with sufficient structural integrity with four sets of bolt and nut lug-fasteners 43. A forehead-rest 96 (FIG. 15) is shown broken away. A full view of it is shown in FIG. 15. Refer to FIG. 7 and FIG. 8 for a description of other referenced components.

FIG. 10 is an orthographic back view of the preferred embodiment. This shows the gear teeth of the vertical-pinion 71 engaging both the right-vertical-rack 35 and the left-vertical-rack 36 gear teeth. It is so open and accessible that a transparent-gear-cover 73 (invisible in this view) is provided to prevent a patient's hair from getting tangled in the gears. The transparent-gear-cover 73 has a height and width matching the vertical-guide 32 and is secured in place with fasteners 75. The forehead-rest 96 is not shown so that the relationship between the pinion 71 and the two racks 35 and 36 can be clearly shown. The horizontal-guide 31 is shown behind the vertical-guide 32. The vertical-pinion 71 is shown held in place on the vertical pinion-axle 55 by the locknut 72.

Figure 11:
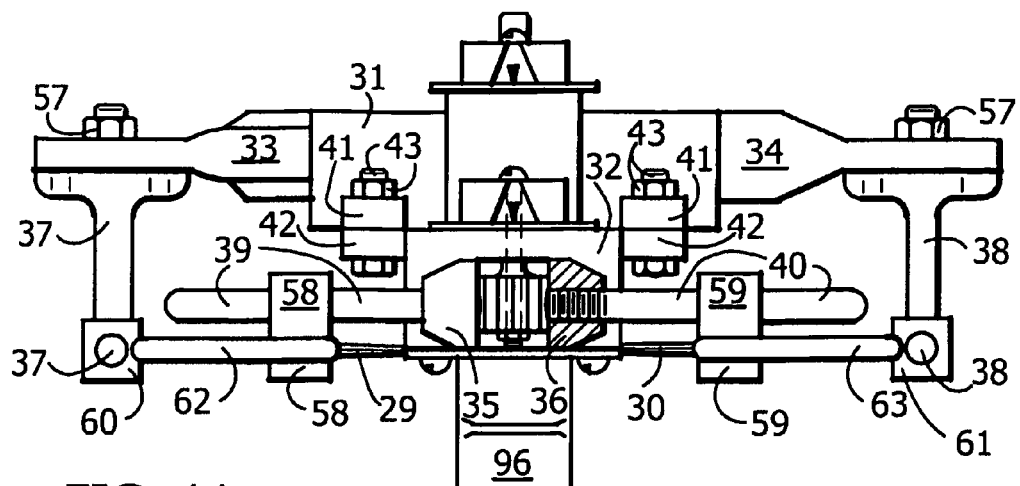
FIG. 11 is an orthographic bottom view of the preferred embodiment employing the principles of the present invention.

FIG. 11 illustrates the bottom view of the preferred embodiment, employing the principles of the present invention. Refer to FIG. 7 and FIG. 8 for a complete description of the components referenced, except the forehead-rest 96 is not referenced in FIG. 7 and FIG. 8. See FIG. 15 for a complete description of the forehead-rest 96.

FIG. 12 Illustrates a partial section view taken through FIG. 7. Components of particular interest in this view are the right-vertical-T-shaped-groove 82 and the left-vertical-T-shaped-groove 83 in which the right-vertical-rack 35 and the left-vertical-rack 36 respectively slide up and down in the vertical-guide 32 in opposite directions as the vertical-adjustment-knob 49 is rotated clockwise and counterclockwise. Due to the connection of the vertical-adjustment-knob 49 to the vertical-pinion 71 through the vertical-pinion-axle 55, the rotational movement of the vertical-pinion 71 mimics the rotation of the vertical-adjustment-knob 49. The vertical-pinion-axle 55 passes through the second-central-hole 90, the second-slip-fit-hole 93 and the second-non-round-hole 92 in the vertical-pinion 71. The vertical-pinion 71 is held in its proper place by the locknut 72.

FIG. 13 illustrates a partial side view taken from FIG. 9. Components of particular interest in this partial view are the ones interconnecting the horizontal-adjustment-knob 50 with the sliding movement of the bottom-horizontal-rack 33 and the top-horizontal-rack 34 within the bottom-horizontal-T- shaped-groove 80 and the top-horizontal-T-shaped groove 81, both within the horizontal-guide 31. The horizontal-pinion-axle 56 passes through the first-central-hole 89 in the center of the horizontal-adjustment-knob 50 and is prevented from rotating within the first-central-hole 89 by the first-set-screw 84 (hidden in this view). The horizontal-pinion-axle 56 continues on through the first-slip-fit-hole 76 in the bearing-plate 86 and on through the first-non-round-hole 91 in the horizontal-pinion 70 and terminating in the bearing-hole 88. The locknut 72 holds the horizontal-pinion 70 in its proper place. Refer to FIG. 7 and FIG. 8 for a complete description of other components referenced.

FIG. 14 illustrates how a right-lens-blank-axis 21 of a right-lens-blank 16 is above a right-frame-visual-axis 14 by a right-vertical-distance 25 as determined by an eye exam employing the principles of the present invention; the right-lens-blank-axis 21 is to the left of the right-frame-visual-axis 14 by a right-horizontal-distance 27 as determined by the same eye exam.

Likewise FIG. 14 illustrates how a left-lens-blank-axis 22 of a left-lens-blank 17 is below a left-frame-visual-axis 15 by a left-vertical-distance 26 and the left-lens-blank-axis 22 is to the right of the left-frame-visual-axis 15 by a left-horizontal-distance 28 as determined by the same eye exam.

It can now be seen that with this prescription, a commercially available edging machine can be used to grind the right-lens-blank 16 to fit a right-lens-cut-line 20 and the left-lens-blank 17 to fit a left-lens-cut-line 19 so both lenses can be mounted in eyeglass-frames 18 for use by a Diplopic patient for improved reading ability.

FIG. 15 illustrates the forehead-rest 96 that steadies the embodiment in relation to the patient's eyes 74. It is attached with adhesive to the transparent gear-cover 73 (hidden by the left-vertical-rod 38). The forehead-rest 96 is positioned and fixedly attached to the patient side of the apparatus to press against the patient's forehead when the eyes align with the centers of a pair of plano lenses having crosshairs wherein the forehead-rest 96 is constructed of a soft spongy material covered with soft vinyl.

FIG. 16 illustrates a rigid adjustable eyeglass frame (Front View, Side View and partial enlarged view) for holding stationary-lenses 98 for patients who require a negative (−) lens in addition to a prism lens to obtain the necessary magnification for the intended purpose. The eyeglass-frame 105 has on each end a PD-millimeter-scale 104 ranging from approximately 25 mm to 35 mm to accommodate most PDs. A rigid integral central-extension 106 extends upward to the level of a horizontal-slot 97 at which point a rigid integral horizontal-fitting 107 is sized to snuggly fit into the horizontal-slot 97 located near the bottom of the Vertical-guide 32 (doctor's side). The lens 98 is held in front of the patient's eye by a lens-holder 99 that has a groove that snuggly fits the lens with sufficient tension to prevent the lens falling out. Integral to the lens-holder 99 is a rigid extension 100 that projects outward away from the patient and then vertically to an integral sleeve 102 that freely slides along the eyeglass-frame 105, when a thumbscrew 108 is loose. The sleeve 102 has a window 101 on the doctor's side that allows full view of a sufficient portion of the PDmillimeter-scale 104. The sleeve 102 has a PD-index 103 at the bottom edge of the eyeglass-frame 105 for the purpose of aligning the PD index 103 with the appropriate PD on the PD-milllimeter-scale at which time the thumbscrew 108 is tightened.

Figure 17:
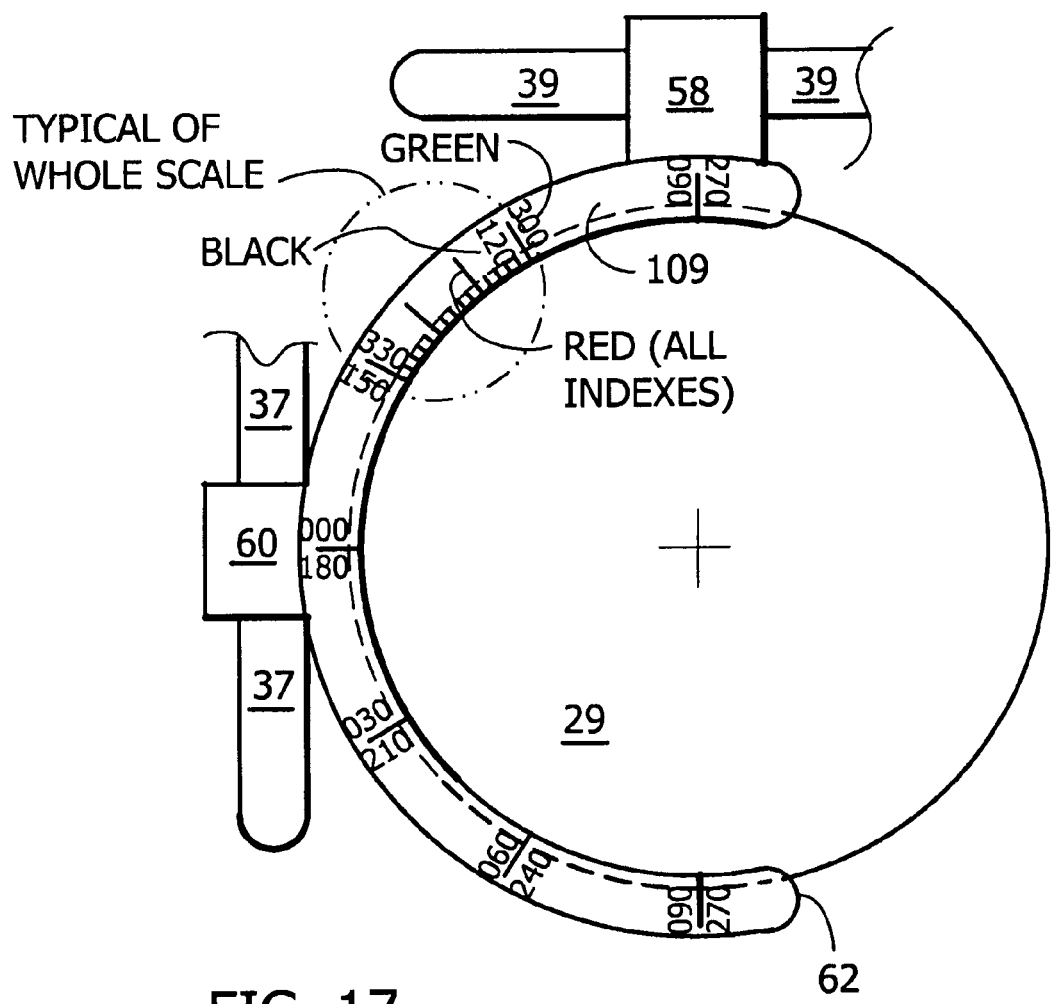
FIG. 17 is an enlarged view of the OD lens holder showing, in detail, the radial scale divided into two degree increments.

FIG. 17 is an enlarged view of the OD lens holder showing, in detail, the radial scale divided into two degree increments. A simple eye test can reveal the "angle" of the displacement of images seen by a Diplopic patient. The angle for the OS will be 180 degrees from the OD angle. This allows the doctor to insert a decentered lens into the lens-holder 62 and rotate it until the black index is aligned with the angle found (black number) by the eye test. If no such black angle exists on the OD-scale 109 then rotate the lens until the green index on the lens aligns with the angle that is identified with green numbers. Mathematically add the H & V components (based on the angle) of the decentered lens to the H & V components found by the horizontal-scale 48 and vertical-scale 47 according to the User-instructions 44 printed on the vertical-guide 32 after the Rx has been fine tuned using the horizontal-adjustment-knob 50 and vertical-adjustment-knob 49 controls. With these combined H & V values an Rx can be calculated and written in whatever notation is desired for the OD. Ultimately the OS will have values equal to but opposite the H & V values of the OD.

Figure 18:
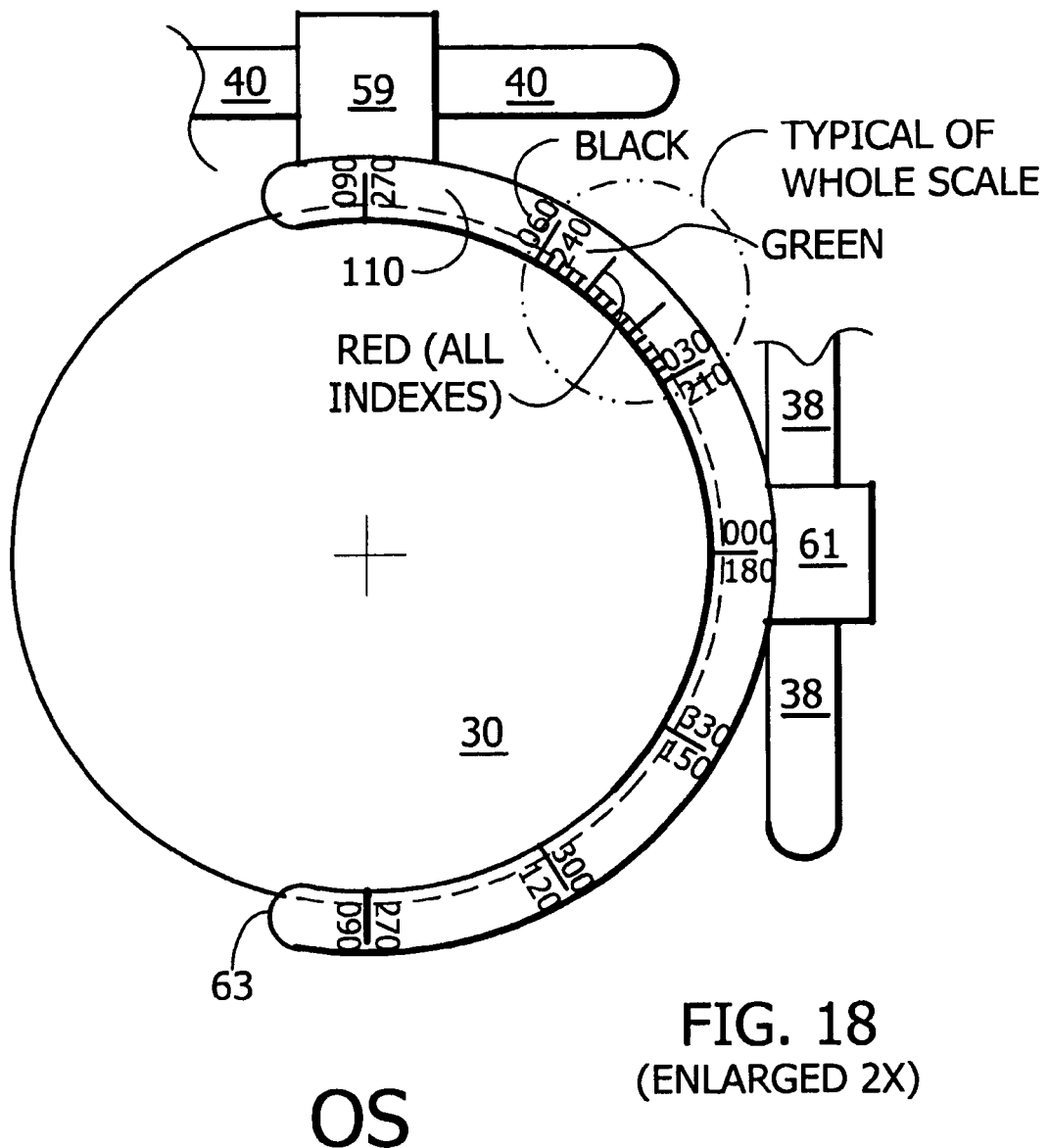
FIG. 18 is an enlarged view of the OS lens holder showing, in detail, the radial scale divided into two degree increments.

FIG. 18 is an enlarged view of the OS lens holder showing, in detail, the radial scale divided into two degree increments. Based on information already known (from FIG. 17 above) the doctor can insert a decentered lens into the lens-holder 63 and rotate it until the black index is aligned with the angle found (black number) by the eye test. If no such black angle exists on the OS-scale 110 then rotate the lens until the green index on the lens aligns with the angle that is identified with green numbers. Mathematically add the H & V components (based on the angle) of the decentered lens to the H & V components found by the horizontal-scale 48 and vertical-scale 47 according to the User-instructions 44 printed on the vertical-guide 32 after the Rx has been fine tuned using the horizontal-adjustment-knob 50 and vertical-adjustment-knob 49 controls. With these combined H & V values an Rx can be calculated and written in whatever notation is desired for the OS.

The foregoing merely illustrates the principles of the invention. For example, although the means for positioning the lens in front of the patient's eyes in the illustrated embodiment are rack and pinion gears, other means are possible such as threaded screws or servo motors. The millimeter scales could be a different unit. The circular scales and the indexes on round knobs could be changed to linear scales affixed to the racks with single indexes affixed to the vertical guide and the horizontal guide. The sliding fit of the four rod bushings could be replaced with linear-ball bearings.

It will thus be appreciated that those skilled in the art will be able to devise numerous alternative arrangements that, while not shown or described herein, employ the principles of the invention and thus are within its spirit and scope.

What is claimed is:

1. An apparatus comprising:
an infinitely variable graduated horizontal control that moves a pair of lens holders slowly in front of a patients eyes equal distances but opposite directions and, independently from the horizontal control, an infinitely variable graduated vertical control that slowly moves the lens holders in front of the patients eyes equal distances but opposite directions; wherein the apparatus finds and defines, for Diplopic and AMD patients who have double vision, a location of each axis of a pair of spherical lens-blanks (of appropriate diopter) relative to a visual-axis of each respective eye of the patient, whereat each respective lens-axis is offset from the visual-axis of each respective eye by an infinitely variable graduated horizontal control that slowly moves the lens blanks equal distances but opposite directions (H-coordinates) in front of the patient's eyes and by an infinitely variable graduated vertical control that slowly moves the lens blanks equal distances but opposite directions (V-coordinates) in front of the patient's eyes that causes a required induced prism that in turn causes the patient viewing through the lens-blanks to see single vision; the H-V coordinates, combined with the diopter, become a required Rx that is converted by the user instructions to BI, BO, BU, BD notation; and a pair of spherical stationary-lenses of appropriate minus diopter are added, in the case of a patient whose eyes require such for near or far focusing, to be used in combination with the prism lenses so that the total magnification is compatible with the patient's eyes.

2. An apparatus for finding and defining an Rx for eyeglass prism lenses for Diplopic and AMD patients who have double vision comprising:

two complete sets of centered spherical lens-blanks (sized to fit lens-holders) for use in conjunction with the apparatus, comprising a complete range of plus (+) and minus (−) diopters, each of which are centered lenses with a segment removed to prevent interference when the lenses are moved toward each other;

two complete sets of decentered lens-blanks (one set sized for each lens holder), for use in conjunction with the apparatus comprising a complete range of plus (+) and minus (−) diopters for each of at least three sub-sets of decentered lenses of varying degrees of decentration up to and a maximum of 70 mm of decentration;

a black-identifying-index at the intersection of the center-line and the base of each decentered lens;

a green-identifying-index on the center-line at the edge opposite the base of each decentered lens;

two complete sets of spherical stationary-lens-blanks (edged to fit stationary-lens-holders) comprising a complete range of centered minus (−) diopter lenses for use in conjunction with the apparatus;

a means for steadying the apparatus in relation to the patient's eyes;

a means for facilitating the calculation of a prism Rx based upon the radial orientation of a decentered lens within a lens-holder;

a means for holding and positioning a pair of lens-blanks, having correct diopters for the patient, so that the center of each respective lens-holder is offset from a visual-axis of each respective eye by a horizontal and a vertical decentration (H-V coordinates) that causes a required induced prism that in turn causes the double images that the patient sees to fuse;

a means for holding a pair of stationary-lens-blanks so that the lenses' visual axes coincide with the axes of the patient's eyes that require a second spherical lens of an appropriate minus (−) diopter to accomplish a desired total magnification effect for near or far focusing when combined with the magnification/induced prism of the lens-blanks;

a means for indicating in centimeters the H-V coordinates of the center of each respective lens-holder in relation to the axis of each respective patient's eye;

a means for zeroing the apparatus at a point of horizontal movement of the lens-holders whereat a spacing of the centers of the lens-holders matches a PD of the patient's eyes; the means for steadying the apparatus in relation to the patient's eyes includes a forehead-rest constructed of a vinyl covered molded soft spongy material positioned and fixedly attached to the patient's side of the apparatus to press against the patient's forehead when the eyes' axes align with the centers of a pair of crosshairs; the means for facilitating the calculation of a prism Rx based upon the radial orientation of decentered lenses within the lens-holders, the means comprising:

radial indexes with numbers ranging from 0 to 360 degrees, in 30 degree increments, on the Doctor's side of the lens holders where the numbers on the OD lens holder from 0 to 090 and 270 to 360 degrees are in one color and from 090 to 270 are in a second color but sharing the same indexes that are in a third color, in which the appropriate decentered lens is rotated to the angle that best suits the patient;

radial indexes on the OS lens holder where the numbers from 090 to 270 are in one color and from 270 to 360 and from 0 to 090 are in a second color but sharing the same indexes that are in a third color, in which the appropriate decentered lens is rotated to the angle that best suits the patient, after the aforementioned rotation of both lenses, further fine tuning is accomplished by manual rotation of the horizontal and vertical adjustment knobs; and calculations based on the BU, BD, BI, BO notation derived from the H-V coordinates and, using equations known to those skilled in the art, mathematically combine BU, BD, BI and BO with the induced prism created by the decentration of the lenses plus the effect of the rotation of the decentered lenses, to arrive at a prism lens Rx expressed in 360.

3. The invention of claim 2 in which the means for holding and positioning a pair of lens-blanks, having correct diopters for the patient, so that the center of each respective lens-holder is offset from a visual-axis of each respective eye by a horizontal and a vertical decentration (H-V coordinates) that causes a required induced prism that in turn causes the double images that the patient sees to fuse, the means comprising:

a horizontal-guide that has a bottom-horizontal-T-shaped-groove and a top-horizontal-T-shaped-groove facing each other and running parallel to each other and spaced apart far enough from each other to accommodate a bottom-horizontal-rack and a top-horizontal-rack;

two racks each having a T-shaped cross section that engages each respective T-shaped-groove in the horizontal-guide in which the gear teeth face each other and a horizontal-pinion is juxtaposed between the bottom-horizontal-rack and the top-horizontal-rack so that rotating a horizontal-pinion-axle rotates the horizontal-pinion that engages the bottom-horizontal-rack and the top-horizontal-rack and causes them to slide equal distances but in opposite directions within the bottom-T-shaped-groove and the top-T-shaped-groove in the horizontal-guide;

a right-vertical-rod fixedly attached to a right end of the bottom-horizontal-rack and vertically slidably connected to a right-lens-holder whereby horizontal motion of the bottom-horizontal-rack imparts an equal motion to the right-lens-holder;

a left-vertical-rod fixedly attached to a left end of the top-horizontal-rack and vertically slidably connected to a left-lens-holder whereby horizontal motion of the top-horizontal-rack imparts an equal motion to the left-lens-holder;

a vertical-guide fixedly attached to and at right angles to the horizontal-guide, in which the vertical-guide has a right-vertical-T-shaped-groove and a left-vertical-T-shaped-groove facing each other and running parallel to each other and spaced apart far enough to accommodate a right-vertical-rack and a left-vertical-rack;

two racks, each having a T-shaped cross section that engages the right-vertical-T-shaped-groove and the left-vertical-T-shaped-groove in the vertical-guide in which the gear teeth face each other and a vertical-pinion is juxtaposed between the right-vertical-rack and the left-vertical-rack so that rotating a vertical-pinion-axle rotates the vertical-pinion that engages the right-vertical-rack and the left-vertical-rack and causes them to slide equal distances but in opposite directions within the right-vertical-T-shaped-groove and the left-vertical-T-shaped-groove in the vertical-guide;

a right-horizontal-rod fixedly attached to a bottom end of the right-vertical-rack and horizontally slidably connected to the right-lens-holder whereby vertical motion of the right-vertical-rack imparts an equal motion to the right-lens-holder; and a left-horizontal-rod fixedly attached to a bottom end of the left-vertical-rack and horizontally slidably connected to the left-lens-holder whereby vertical motion of the left-vertical-rack imparts an equal motion to the left-lens-holder.

4. The invention of claim 3 in which the means for holding a pair of stationary-lens-blanks so that the lenses' visual axes coincide with the axes of the patient's eyes that require a second spherical lens of an appropriate minus (−) diopter to accomplish a desired total magnification effect for near or far focusing when combined with the magnification/induced prism of the lens-blanks, the means comprising:

a horizontal slot at the bottom center of the vertical-guide, with an opening on the side facing the doctor, in which the slot is shaped to accept a horizontal-fitting at a top end of a central-extension of an eyeglass-frame;

the horizontal rigid eyeglasses-frame long enough to span the PD of the eyes of an adult and having an integral flat central-extension at the midpoint that projects vertically to the bottom of the vertical-guide, whereat a horizontal-fitting extends horizontally with a size and shape that will slide into the horizontal-slot of similar dimensions formed into the base of the vertical-guide, having a fit that requires a deliberate manual grasp to insert and extract the eyeglasses-frame from the vertical-guide;

a linear PD-millimeter-scale on each end of the eyeglasses frame on the doctor's side indicates PD ranging from about 25 mm to about 35 mm for each eye; and two stationary-lens-holders, each slidably connected to an end of the eyeglasses-frame where each stationary-lens-holder has a semi-circular shape that has a groove adapted to accept various lenses and with sufficient spring tension to prevent the lens falling out in normal use, and further each has an integral extension at the top that slidably connects to the eyeglasses-frame by way of a sleeve, integral to the top end of each extension, that slides over the eyeglasses-frame and has a thumbscrew at the top for the purpose of making contact with the eyeglasses-frame, and further each sleeve has a window on the doctor's side so that each PD-millimeter-scale on the eyeglasses-frame is visible through each window and a required PD-millimeter-index can be aligned with a single PD-index located at the bottom edge of the center of each window, at which point tightening each thumbscrew holds each single PD-index firmly in alignment with a required PD-millimeter-index on each side of the eyeglasses-frame.

5. The invention of claim 4 in which the means for indicating in centimeters the H-V coordinates of the center of each respective lens-holder in relation to the axis of each respective patient's eye, the means comprising:

a horizontal-adjustment-knob for the H coordinate fixedly attached to the horizontal-pinion-axle so that rotation of the horizontal-adjustment-knob causes equal rotation of the horizontal-pinion;

a circular color coded horizontal-scale centered on the horizontal-pinion-axle and restrained from rotating by a zeroing-thumbscrew and a washer thus clamping the horizontal-scale between the washer and a bearing-plate that is fixedly attached to the horizontal-guide whereby colored numbers on the horizontal-scale coordinate with colors in a user-instructions therein indicating whether a decentration amount on the horizontal-scale that is aligned with a horizontal-index on the horizontal-adjustment-knob represents centimeters of induced prism Base-In (BI) or Base-out (BO) for each respective lens-holder;

a vertical-adjustment-knob for the V-coordinate fixedly attached to the vertical-pinion-axle so that rotation of the vertical-adjustment-knob causes equal rotation of the vertical-pinion; and a circular color coded vertical-scale centered on the vertical-pinion-axle and fixedly attached to the vertical-guide whereby colored numbers on the vertical-scale coordinate with colors in the user-instructions therein indicating whether a decentration amount on the vertical-scale that is aligned with a vertical-index on the vertical-adjustment-knob represents centimeters of induced prism Base-Up (BU) or Base-Down (BD) for each respective lens-holder.

6. The invention of claim 5 in which the means for zeroing the apparatus at a point of horizontal movement of the lens-holders whereat a spacing of the centers of the lens-holders matches a PD of the patient's eyes, the means comprising:

the circular color coded horizontal-scale free to rotate about the horizontal-pinion-axle; and the zeroing-thumbscrew with the washer juxtaposed so that tightening the zeroing-thumbscrew clamps the horizontal-scale between the washer and the bearing-plate thereby preventing further rotation of the horizontal-scale, whereupon such clamping action is performed at a point in an examination of a patient's eyes when a spacing of a right-crosshairs and a left-crosshairs, hingedly connected to corresponding movable-lens-holders, coincide with the PD of the patient's eyes and the horizontal-scale is rotated until zero on the horizontal-scale is aligned with the horizontal-index printed on the horizontal-adjustment-knob that is fixedly attached to the horizontal-pinion-axle.

* * * * *